(12) United States Patent
Jimenez et al.

(10) Patent No.: US 8,763,194 B2
(45) Date of Patent: Jul. 1, 2014

(54) ORAL CARE IMPLEMENT

(75) Inventors: Eduardo Jimenez, Manalapan, NJ (US);
Andreas Wechsler, Zell am See (AT);
Joachim Storz, Zell am See (AT);
Raimund Klausegger, Vienna (AT)

(73) Assignee: Colgate-Palmolive Company, New York, NY (US)

( * ) Notice: Subject to any disclaimer, the term of this patent is extended or adjusted under 35 U.S.C. 154(b) by 19 days.

(21) Appl. No.: 13/518,423

(22) PCT Filed: Dec. 23, 2009

(86) PCT No.: PCT/US2009/069382
§ 371 (c)(1),
(2), (4) Date: Jun. 22, 2012

(87) PCT Pub. No.: WO2011/078860
PCT Pub. Date: Jun. 30, 2011

(65) Prior Publication Data
US 2012/0266400 A1  Oct. 25, 2012

(51) Int. Cl.
*A46B 9/04* (2006.01)
*A46B 9/06* (2006.01)
*A46B 15/00* (2006.01)

(52) U.S. Cl.
USPC .............. 15/110; 15/167.1; 15/188; 601/139; 601/141

(58) Field of Classification Search
USPC ................... 15/104.94, 110, 167.1, 187, 188; 601/139, 141; 433/114, 125, 141–142, 433/166; 401/270, 265–266
See application file for complete search history.

(56) References Cited

U.S. PATENT DOCUMENTS

| 1,268,544 | A |   | 6/1918 | Cates |
|---|---|---|---|---|
| 1,405,279 | A |   | 1/1922 | Cassedy |
| 1,661,713 | A | * | 3/1928 | Barker ............................ 15/188 |
| 1,993,763 | A |   | 3/1935 | Touchstone |
| 2,946,072 | A | * | 7/1960 | Filler et al. ....................... 15/110 |
| 5,604,951 | A |   | 2/1997 | Shipp |
| 5,735,011 | A |   | 4/1998 | Asher |
| 6,993,804 | B1 | * | 2/2006 | Braun et al. ..................... 15/110 |

(Continued)

FOREIGN PATENT DOCUMENTS

| JP | 2000000119 A | * | 1/2000 | ............... A46B 9/04 |
|---|---|---|---|---|
| JP | 2000004945 A | * | 1/2000 | ............... A46B 9/04 |
| WO | WO 98/18364 |   | 5/1998 |   |
| WO | WO 2004/028235 |   | 4/2004 |   |

OTHER PUBLICATIONS

JP2000000119A (Abstract), 2000.*
JP2000004945A (Abstract), 2000.*

(Continued)

*Primary Examiner* — Mark Spisich
*Assistant Examiner* — Andrew A Horton
(74) *Attorney, Agent, or Firm* — Ryan M. Flandro

(57) ABSTRACT

An oral care implement such as a toothbrush includes a head and a plurality of tooth cleaning elements supported by the toothbrush head. The tooth cleaning elements preferably include an elastomeric polishing element defining an elevated dentifrice retaining recess spaced above the toothbrush head for holding dentifrice. In one embodiment, the recess may be configured as an annular groove. Preferred embodiments of the recess include a partially or completely closed bottom portion to support and minimize loss of dentifrice during brushing. In some embodiments, the polishing element may be collectively formed from a plurality of Y-shaped polishing members.

22 Claims, 7 Drawing Sheets

(56) References Cited

U.S. PATENT DOCUMENTS

| | | | |
|---|---|---|---|
| 2003/0077107 A1* | 4/2003 | Kuo | 401/278 |
| 2003/0229959 A1* | 12/2003 | Gavney et al. | 15/117 |
| 2004/0154112 A1 | 8/2004 | Braun et al. | |
| 2004/0158948 A1* | 8/2004 | Sander et al. | 15/188 |
| 2004/0200016 A1 | 10/2004 | Chan et al. | |
| 2005/0166343 A1* | 8/2005 | Gavney, Jr. | 15/110 |
| 2008/0184511 A1 | 8/2008 | Brown et al. | |
| 2009/0255077 A1* | 10/2009 | Mori et al. | 15/167.1 |
| 2011/0047734 A1* | 3/2011 | Jimenez et al. | 15/167.1 |

OTHER PUBLICATIONS

International Search Report and Written Opinion in International Application No. PCT/US09/069382, mailed Oct. 8, 2010.

Written Opinion in International Application No. PCT/US09/069382, mailed Feb. 7, 2012.

* cited by examiner

_US 8,763,194 B2_

ORAL CARE IMPLEMENT

This application is a national stage entry under 35 U.S.C. §371 of International Patent Application No. PCT/US2009/069382, filed 23 Dec. 2009, the contents of which are incorporated herein by reference.

FIELD

The present invention relates to oral care implements, and more particularly to a toothbrush with tooth cleaning elements.

BACKGROUND

Oral care implements such as toothbrushes are typically used in conjunction with a dentifrice for cleansing the teeth and/or soft tissue in the oral cavity. The dentifrice or similar oral care product may contain one or more active ingredients which when administered with a toothbrush generally via a brushing action provide an oral health benefit to the user such as removing plaque and debris from the surface of the teeth and/or gums, polishing and whitening the teeth, reducing oral surface bacteria populations, and others.

Conventional toothbrush heads generally contain a plurality of tooth cleaning elements such as bristles which temporarily support the dentifrice during its application to the teeth and/or gums. By design, such bristles usually are formed into tufts containing numerous individual bristle strands (typically made of nylon or another polymer) and are primarily adapted for removing debris. These general purpose bristles are not optimized for polishing and removing stains from tooth surfaces particularly when used with a dentifrice containing whitening and polishing agents. The tips of the individual bristle strands make less than ideal surface area contact with tooth surfaces to achieve the optimum type of polishing action desired to effectively remove stains, and polish and whiten the teeth.

Oral treatment dentifrices such as toothpaste are available in wide variety of formulations including tarter removal/control, whitening, sensitive teeth, enamel protection, and others. In order for the user to obtain maximum benefit from such products, the dentifrice should preferably remain in contact with the teeth during brushing. However, the dentifrice typically migrates either into the mouth of the user from the toothbrush bristles which support the dentifrice, or is forced downwards in between and towards the base of the bristles thereby minimizing the effectiveness of the dentifrice.

A toothbrush head which better supports the dentifrice for application to the teeth during brushing is therefore desired.

SUMMARY

An oral care implement such as a toothbrush according to one embodiment of the present invention includes a plurality of tooth cleaning elements including bristle elements and preferably one or more tooth polishing units configured and adapted to provide enhanced cleaning, polishing, and whitening of the teeth. The polishing unit includes an elevated dentifrice retaining pocket or recess that is vertically spaced and raised above the surface of the toothbrush head and preferably positioned in the active brushing zone of the tooth cleaning elements. In contrast to conventional toothbrush bristle constructions in which the dentifrice merely sits on top of the bristles from which it is readily dislodged during brushing, the elevated retaining recess advantageously is specially configured to cradle the dentifrice for minimizing excessive loss and migration of dentifrice from the active brushing zone. This maximizes contact between the dentifrice and teeth during brushing to enhance the effectiveness of the oral care regimen. The retaining recess may be generally configured in the form of a V-shaped pocket in exemplary embodiments that cradles and supports the dentifrice. In some embodiments, the retaining recess may be configured as a circumferentially extending annular groove disposed in the polishing unit with an upwardly open top and a partially or more preferably completely closed bottom portion to better retain the dentifrice.

In preferred embodiments, the polishing units include elastomeric polishing elements that define the dentifrice retaining recess. The polishing elements may each be comprised of a plurality of polishing members in some embodiments that are concentrically arranged around a common point. In one embodiment, each polishing member may be Y-shaped; however other suitable configurations are possible.

According to one exemplary embodiment, a toothbrush according to present invention includes a toothbrush head defining a longitudinal axis and a plurality of tooth cleaning elements supported by the toothbrush head. The tooth cleaning elements included at least one tooth polishing unit having an elastomeric polishing element. An elevated dentifrice retaining recess is defined by the polishing element which is preferably spaced and raised above the toothbrush head for holding dentifrice. In some embodiments, the polishing element may be comprised of a plurality of individual Y-shaped polishing members. In yet further embodiments, the polishing unit includes a bristle element disposed at least partially, and more preferably completely inside the polishing element for enhanced cleaning, polishing and whitening action.

BRIEF DESCRIPTION OF THE DRAWINGS

The features of the preferred embodiments will be described with reference to the following drawings where like elements are labeled similarly, and in which.

Figure 1:
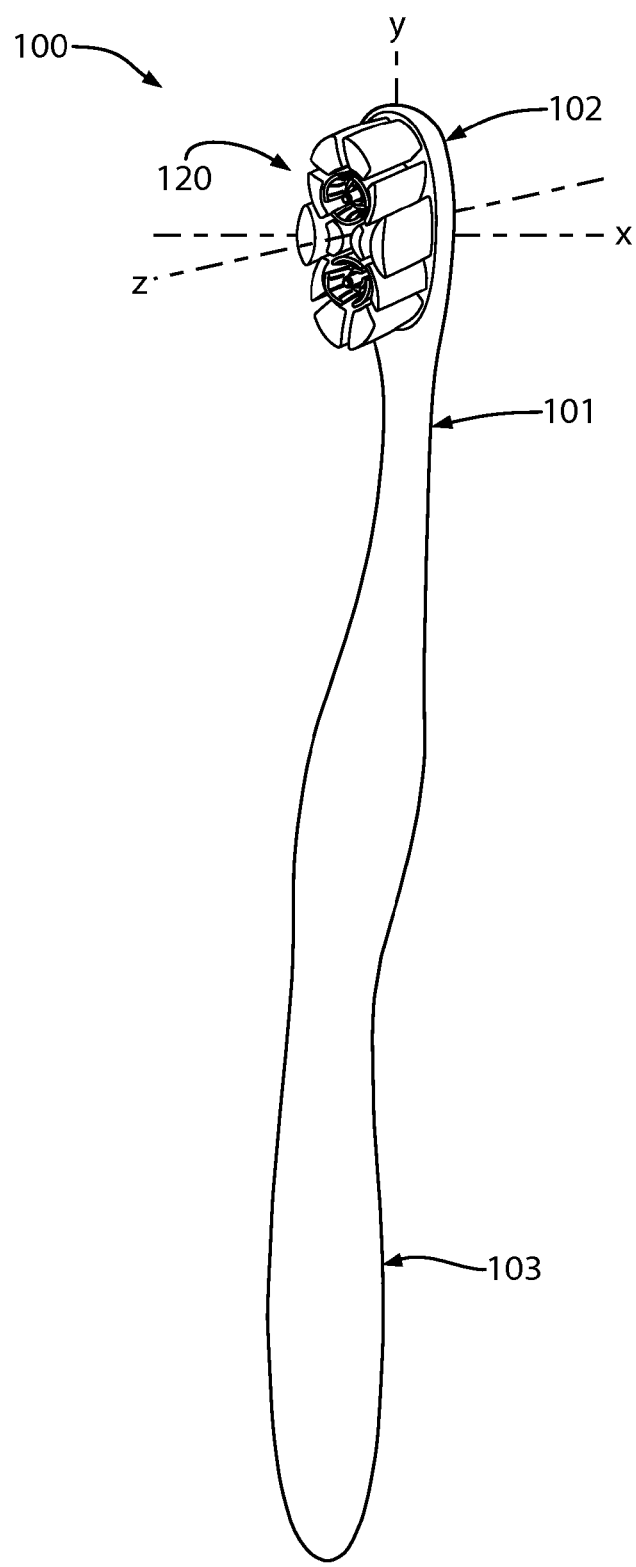
FIG. 1 is a perspective view of a toothbrush according to one exemplary embodiments of the invention.

All drawings are schematic and not actual physical representations of the articles, components or systems described herein, and are further not drawn to scale. The drawings should be interpreted accordingly.

DETAILED DESCRIPTION

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combination of features that may exist alone or in other combinations of features; the scope of the invention being defined by the claims appended hereto.

FIG. 1 depicts one exemplary embodiment of an oral care implement in the form of a toothbrush 100 including a head 102 having a neck portion 101 and a handle 103 for grasping by a user. The handle 103 may be permanently or detachably coupled to the neck portion 101; the latter detachable handle example being suitable for a toothbrush having user-replaceable heads or toothbrush having a replaceable handle with an oral care agent. The handle 103 is generally elongated in shape and may have any suitable ergonomic and aesthetically pleasing configuration dimensioned to gripped by a user. The handle 103 may be formed of one or more suitable materials conventionally used in the art for toothbrush handles including without limitation polymers, rubber, thermoplastic elastomers (TPE), and combinations thereof. Accordingly, the handle 103 may be formed with many different shapes, lengths, and varieties of constructions.

In some embodiments, the handle 103 may form part of a battery-operated toothbrush and include a power source and electric/electronic components. Accordingly, the toothbrush head 102 is not limited in its application to either manual or battery-operated toothbrushes alone. In some embodiments, the handle 103 may include a reservoir having an oral care agent that can be applied to the oral cavity.

Referring to FIGS. 1-5, the toothbrush head 102 includes a front brushing side 104, an opposing rear side 105, two opposing lateral sides 106, 107, a distal end 108, and a proximal end 109 closest to handle 103. A primary oral care region 110 is defined on front brushing side 104 between lateral sides 106 and 107, distal end 108, and proximal end 109. In some embodiments, the rear side 105 may define a secondary oral care region 111 supporting a tongue cleaner and/or other ancillary tooth or soft tissue cleaning elements (not shown). The toothbrush head 102 may have an elongated elliptical or oval shape in one possible embodiment. The neck portion 101 may be tapered and narrower in width than the head 102 to smoothly transition into the handle 103.

Figure 3:
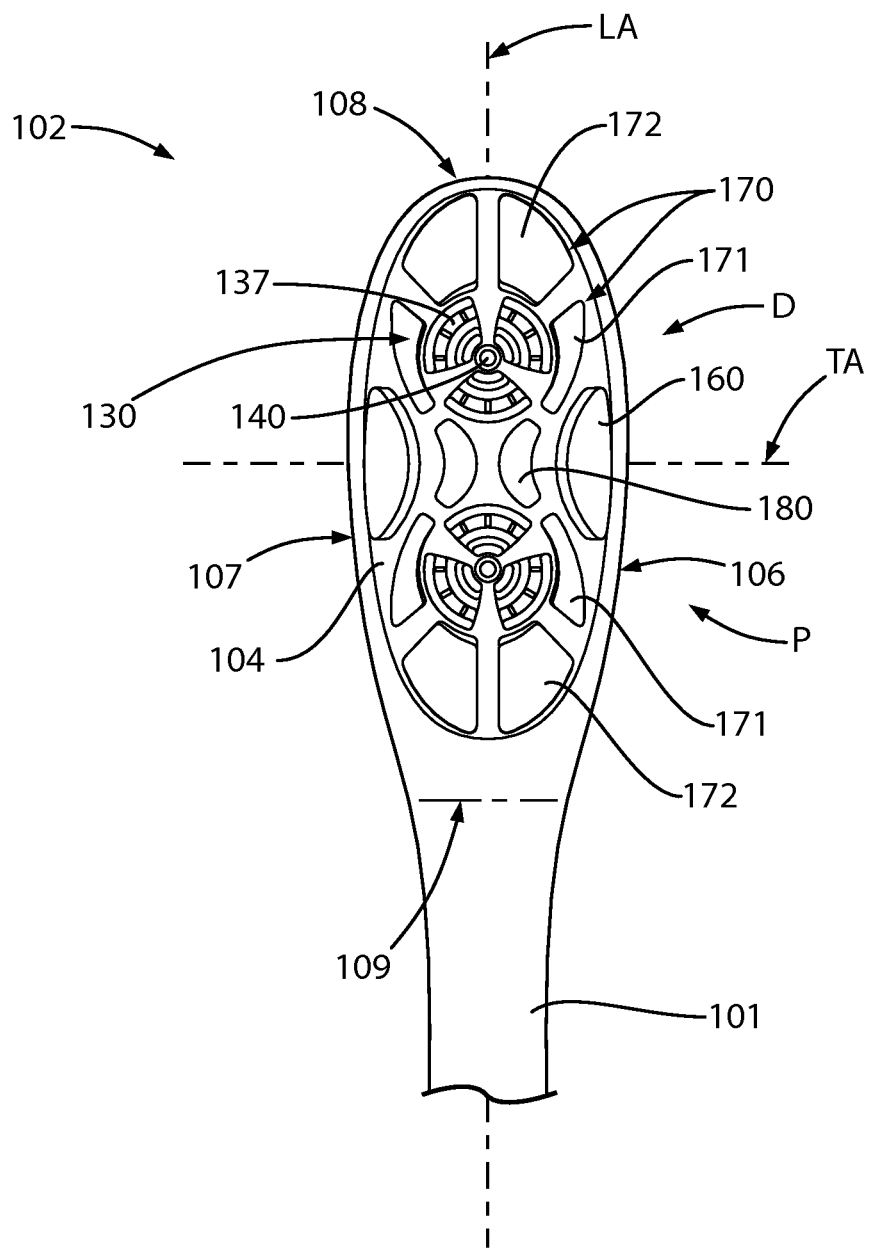
FIG. 3 is a top view of the toothbrush head of FIG. 2.

Referring to FIGS. 1 and 3, an imaginary X-Y-Z coordinate system is identified with respect to the toothbrush head 102 for ease of reference in describing a plurality of tooth cleaning elements 120. A horizontal plane and direction is defined by the X-Y axes (generally parallel to the front brushing side 104 of the toothbrush head 102) and vertical planes and directions are defined by the X-Z and Y-Z axes (generally perpendicular to the front brushing side 104 of the toothbrush head 102). The toothbrush head 102 has a longitudinal axis LA generally coinciding with the X axis and a transverse axis TA perpendicular thereto coinciding with the Y axis and positioned midway between the distal end 108 and the proximal end 109. This divides the oral care region 110 into a proximal treatment half P and distal treatment half D (shown in FIG. 3).

Figure 4:
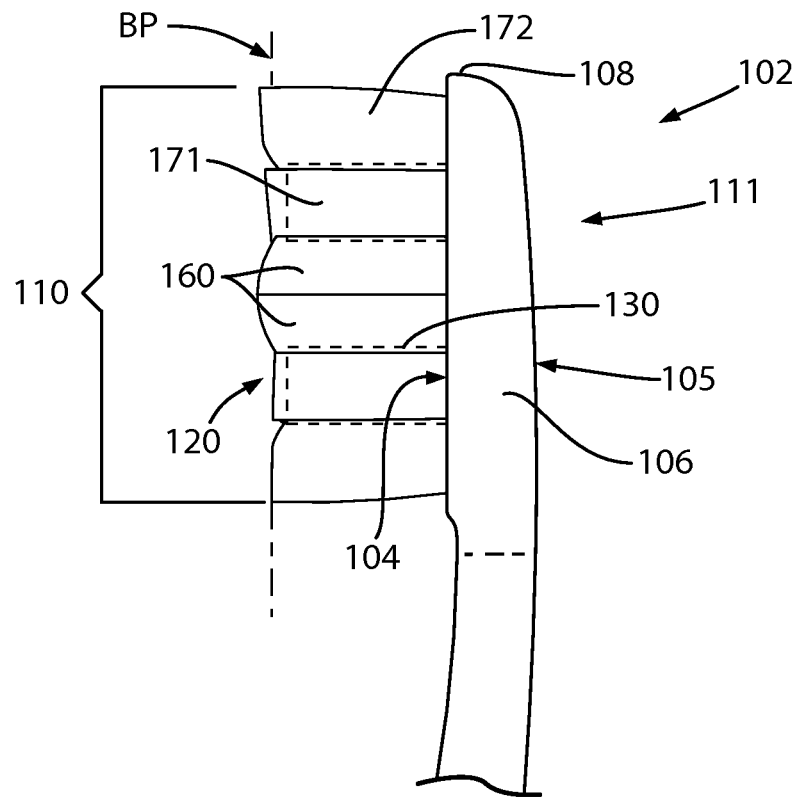
FIG. 4 is a side view of the toothbrush head of FIG. 2.
Figure 5:
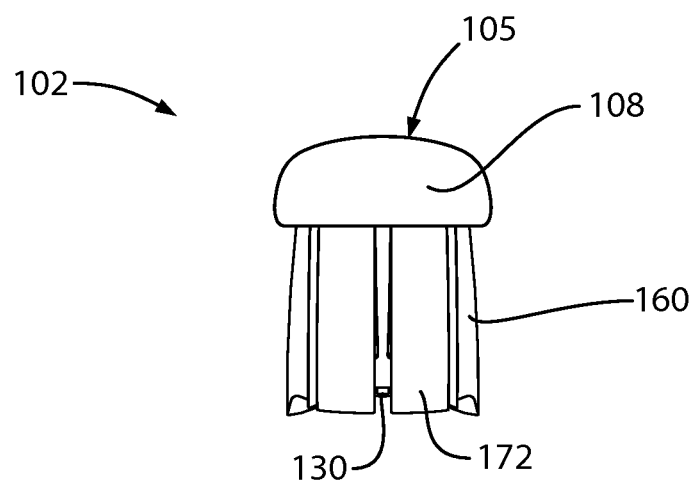
FIG. 5 is a distal end view of the toothbrush head of FIG. 2 (looking towards a handle of the toothbrush)

With continuing reference to FIGS. 1-5, the front side 104 of the oral care region 110 supports a plurality and variety of tooth cleaning elements 120 which are affixed in the toothbrush head 102. The tooth cleaning elements 120 may include a variety of bristle/filament and elastomeric elements. It should be noted that the bristle tufts or elements in the drawings are illustrated in block form without the individual bristle/filament strands being detailed for convenience and clarity so as to not obscure the structure of the bristle elements described herein. As shown in FIG. 4, an imaginary nominal reference brushing plane BP is roughly defined by the tops/free ends of the tooth cleaning elements 120 which is offset from and approximately parallel to the longitudinal axis LA and the front brushing side 104 of the toothbrush head 102 (with variation allowing for varying heights of the cleaning elements 120). The upper portions of the tooth cleaning elements 120 proximate to the brushing plane BP define an active brushing zone in which the majority of contact between the cleaning elements 120 and teeth during brushing occurs. The tooth cleaning elements 120 will now each be described in greater detail.

With continuing reference to FIGS. 1-5, the tooth cleaning elements 120 include at least one flexible and resiliently structured tooth polishing unit 130. As further described herein, the polishing unit 130 has uniquely configured tooth contact surfaces adapted to polish/clean the teeth and to cradle and support the dentifrice D to minimize loss of dentifrice during brushing (see, e.g. FIG. 9). In one exemplary preferred embodiment, the polishing unit 130 includes a resilient/flexible elastomeric tooth polishing element 136 and a bristle element 140 disposed at least partially therein. The elastomeric tooth polishing element 136 includes a vertically elongated supporting shaft or base 131 and a polishing head 132 disposed on top of base 131 which is configured and adapted for holding and supporting the dentifrice, as further described herein in detail. In a preferred exemplary embodiment, the supporting base 131 has a generally but not necessarily precisely columnar or cylindrical shape in configuration. The polishing element 136 has a lower base end 134 for attachment to front brushing side 104 of toothbrush 102 and an opposite upper free end 135 defined by polishing head 132 configured for engaging the teeth.

In one preferred arrangement, at least two polishing units 130 are provided as shown which may be considered a distal polishing unit and a proximal polishing unit located on either side of transverse axis TA, as further described herein. The polishing units 130 are shown schematically in dashed lines in FIG. 3 to show relative position with respect to other tooth cleaning elements to be described herein. The polishing units 130 may be symmetrically positioned and axially aligned with longitudinal axis LA in preferred exemplary embodiments. In other embodiments, one or both polishing units 130 may be positioned off axis with respect to longitudinal axis LA. Some other embodiments may have a single polishing unit 130 positioned at the intersection of longitudinal axis LA and transverse axis TA of toothbrush head 102 at the center of the head or located at some other position on the head. Accordingly, the invention is not limited to the placement or number of polishing units shown in the Figures.

Figure 6:
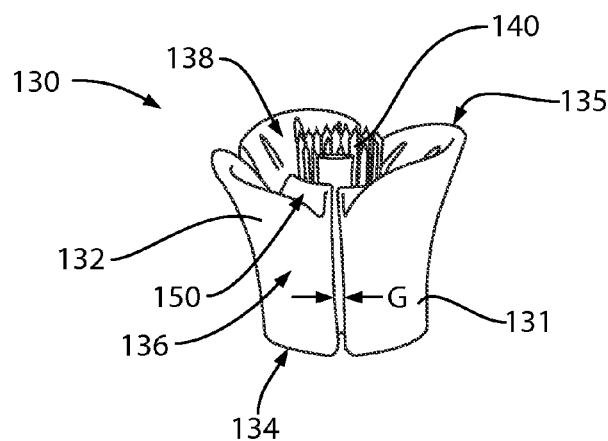
FIG. 6 is a perspective view of a tooth polishing unit of the toothbrush head of FIG. 2.
Figure 7:
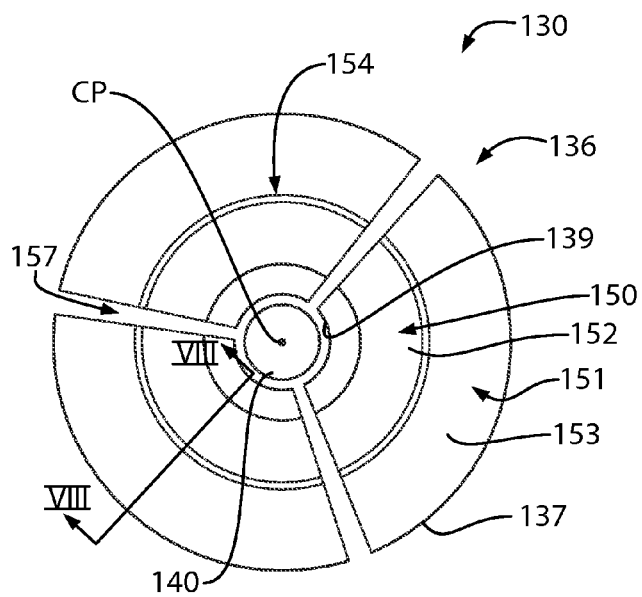
FIG. 7 is a top view of FIG. 6.
Figure 8:
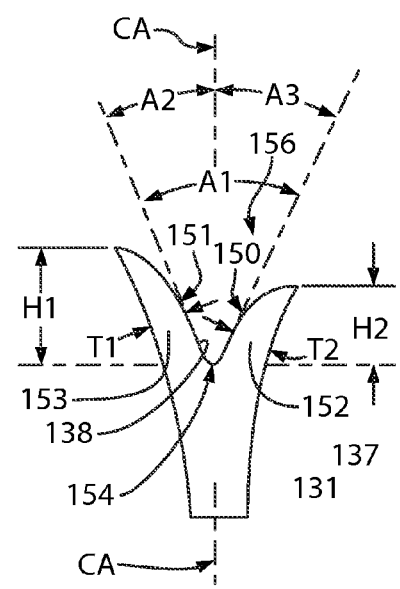
FIG. 8 is a cross-sectional side view of an individual polishing member of the tooth polishing unit of FIG. 6 taken along line 8-8 in FIG. 7.

FIGS. 6 and 7 show a perspective and top view of the polishing element 136 disembodied from the toothbrush head 102 for clarity. FIG. 8 is a cross-sectional vertical side view through the polishing element 136 taken from FIG. 7. In one embodiment, the polishing element 136 preferably has a generally overall but slightly modified cylindrical configuration owing to the outwardly flared polishing head 132 shown in FIG. 8; however, other suitable shapes may be used. The upper ends 135 of the polishing element 136, and in particular the polishing head 132, preferably may be flared outwards as shown to maximize the contact surface area between the polishing head 132 and teeth and therefore optimize the polishing/cleaning effectiveness.

With reference to FIGS. 6-9, the polishing element 136 includes an elevated dentifrice retaining pocket or recess 138 that is vertically spaced and raised above the front brushing side 104 of the toothbrush head 102. The dentifrice retaining recess 138 is specially configured and adapted for holding and supporting the dentifrice D in a manner such that excessive amounts of dentifrice are not lost from the polishing element 136 during brushing. Preferably, to maximize the oral health benefits of the dentifrice being used, the elevated dentifrice retaining recess 138 is positioned in the active brushing zone being generally defined as proximate to the upper portions or half of tooth cleaning elements 120 and the brushing plane BP. In a preferred exemplary embodiment, the retaining recess 138 is formed in the polishing head 132 of polishing element 136. In one possible embodiment shown, the retaining recess 138 may have a generally V-shaped cross sectional shape (see FIG. 8) and defines a correspondingly V-shaped annular groove in the polishing element 136 for holding the dentifrice D (see FIG. 9). This annular groove may be continuous or discontinuous in embodiments where polishing element 136 is comprised of multiple segmented members as further described herein.

The polishing element 136 further defines a central aperture 139 for receiving bristle element 140. The aperture 139 is preferably shaped to complement the cross sectional shape (horizontal) of the bristle element 140. In one exemplary embodiment, as best shown in FIG. 7, the aperture 139 may be circular in top view as further described herein. Other suitable shapes are possible and contemplated.

The elastomeric polishing element 136 may be formed of any suitable flexible and resilient materials having a shape memory that are conventionally used in the art for making such elements. In some embodiments, without limitation for example, the polishing element 136 may be made of rubber or TPE. In a preferred embodiment, the polishing member 136 including supporting shaft or base 131 and polishing head 132 are formed as integral parts of a unitary elastomeric structure which may be molded such as by injection molding in a single step in a conventional manner. In other embodiments, the polishing head 132 may be molded separately and attached to the supporting base 131. Accordingly, the invention is not limited to either construction.

The polishing element 136 may be a single unitary molded elastomeric structure, or in preferred exemplary embodiments may be comprised of two or more separate individual polishing members 137 that may be assembled and arranged in spaced but generally close proximity to collectively form the polishing element 136, as best shown in FIGS. 2, 3, 6, and 7. The polishing members 137 may each individually be formed of the same exemplary types of materials and constructed in a similar manner to polishing element 136 described above. Preferably, the polishing members 137 are spaced sufficiently to define the central aperture 139 for receiving the bristle element 140.

Referring to FIGS. 2, 3, 6, and 7, the tooth polishing element 136 in one preferred embodiment may include three elastomeric tooth polishing members 137 as best shown in FIGS. 6 and 7. More or less polishing members 137 may be provided in other embodiments. The tooth polishing members 137 are arranged proximate to each other and concentrically around a central point CP in circumferentially spaced relation to each other on toothbrush head 102. It will therefore be appreciated that the polishing members 137 of each polishing element 136 need not define a continuous upper and outer circumferential edge at free ends 135 of the polishing element in a preferred embodiment, but instead may be interrupted by circumferential slots or gaps 157 in some embodiments when the polishing element 136 is constructed of two or more separate polishing members 137 (see, e.g. FIG. 7). This segmented structure advantageously provides maximum flexibility to polishing members 137 and polishing element 136 overall. In preferred embodiments, however, adjacent portions of polishing members 137 (e.g. particularly lower portions of each polishing head 132 adjoining their respective supporting base 131) may be spaced relatively closely together circumferentially to minimize such slots or gaps 157 to help prevent excessive amounts of dentifrice held in the annular dentifrice retaining recess 138 from escaping in between the polishing members 137. It is well within the ambit of those skilled in the art to determine appropriate circumferential spacing of the polishing members 137 without undue experimentation to maximize flexibility while minimizing dentifrice loss.

Figure 12:
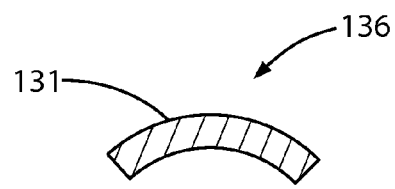
FIG. 12 is a cross-sectional view of a supporting base of the polishing member of FIG. 9 taken along line 12-12 therein.

With continuing reference to FIGS. 6-8, each polishing member 137 preferably has an overall Y shape generally (in vertical cross section) and forms one of three constituent parts that collectively make the polishing element 136. With additional reference to FIG. 9, each polishing member 137 includes a dentifrice retaining recess 138 which may be in the form of a preferably V-shaped groove having an arcuate shape in plan or top view. This V-shape beneficially conserves valuable limited space on the toothbrush head 102 allowing for incorporation of various other type tooth cleaning elements while concomitantly providing for improved support and retention of the dentifrice therein. When each polishing member 137 is assembled to the toothbrush head 102, the arcuately shaped V-grooves combine to form an annular circumferential groove or retaining recess 138 as best shown in FIG. 7. In preferred embodiments, as best shown in cross-section FIG. 12 taken from FIG. 9, the supporting base 131 of each polishing member 137 that lies proximate to the end 134, and preferably at the end 134 itself, may have an arcuately shaped horizontal cross section. When the polishing members 137 are assembled to the toothbrush head 102 and concentrically oriented and spaced around central point CP, they combine to form a polishing element 136 having a generally circular pattern in top view (see FIG. 7). Advantageously, this provides multi-directional cleaning and polishing regardless of the brushing direction employed by the toothbrush user. In this arrangement, it will be appreciated that the dentifrice retaining recess 138 will form a circumferentially-extending discontinuous annular groove with gaps 157 formed between adjacent polishing members 137. In other embodiments where the polishing element 136 is molded formed as a single unitary structure (not shown), or alternatively formed by tightly abutting polishing members 137 together, the annular groove would be circumferentially continuous or nearly continuous.

With continuing reference to FIGS. 6-9, the V-shaped dentifrice retaining recess 138 may be defined by two opposing generally vertical tooth polishing and dentifrice polishing surfaces 150 and 151 formed respectively on an inner and an outer branched portion 152, 153. The inner branched portion 152 and the outer branched portion 153 protrude upwards from the common supporting base portion 131 of each polishing member 137. The polishing surfaces 150, 151 and the retaining recess 138 defined by the branched portions 152, 153 are preferably spaced and elevated above the front brushing side 104 of the toothbrush head 102 as shown, to position the dentifrice in the active brushing zone near the upper portions of the tooth cleaning element 120 and the brushing plane BP. The polishing surfaces 150, 151 are adapted for contacting the teeth, and in some exemplary embodiments may optionally include additional tooth cleaning/polishing appurtenances such as a plurality of raised ribs 155 (best shown in FIG. 9) for improved tooth cleaning/polishing action.

Figure 9:
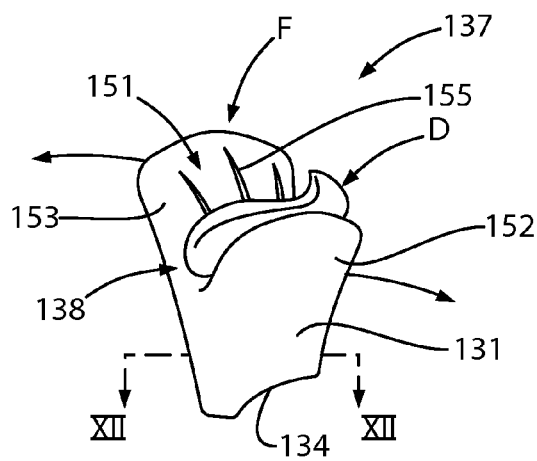
FIG. 9 is a perspective view of an individual polishing member of FIGS. 6-8.

In one preferred exemplary embodiment, as best shown in FIGS. 8 and 9, the inner branched portion 152 and the outer branched portion 153 are oriented in upwardly diverging relationship to each other. The upper free end 135 of the outer branched portion 153 preferably flares outwards from the central point CP, and the upper free end 135 of the inner branched portion 152 preferably is vertical or may flare inwards towards the central point CP. Since the polishing surfaces 150 and 151 defined on the branched portions 152 and 153 respectively serve the dual purpose of both retaining dentifrice and polishing the teeth during brushing, the branched portions 152 and 153 preferably are not oriented completely vertically (i.e. 90 degrees or perpendicular to front brushing side 104 of toothbrush head 102). Instead, as noted above, the branched portions 152 and 153 preferably are angled and flare slightly inwards or outwards respectively from a vertical central axis CA of each polishing member 137 at angles A3 and A2 respectively (see FIG. 6) so that surfaces 150 and 151 have both a horizontally extending and vertically extending component. This configuration beneficially enhances tooth cleaning and polishing.

With continuing reference to FIGS. 8 and 9, the branched portions 152 and 153 are radially spaced apart by an angle A1 to form retaining recess 138 which preferably faces upwards away from toothbrush head 102 (see FIG. 8). Angle A1, which is the sum of angles A2 and A3 is preferably less than about 180 degrees to prevent excessive outwards loss of dentifrice during brushing.

With continuing reference to FIGS. 8 and 9, the retaining recess 138 preferably has an upwardly open top 156 and an at least partially closed bottom 154 adapted for receiving and supporting a ribbon of dentifrice D such as toothpaste. In preferred embodiments, without limitation, the bottom 154 is completely closed as shown for example in FIGS. 8 and 9. Advantageously, the upwardly extending polishing surfaces 150, 151 and closed bottom 154 minimize loss of dentifrice from the retaining recess 138. This keeps the dentifrice in the active brushing zone longer during brushing to maximize contact between the dentifrice and teeth for better cleaning and polishing effectiveness.

Figure 13:
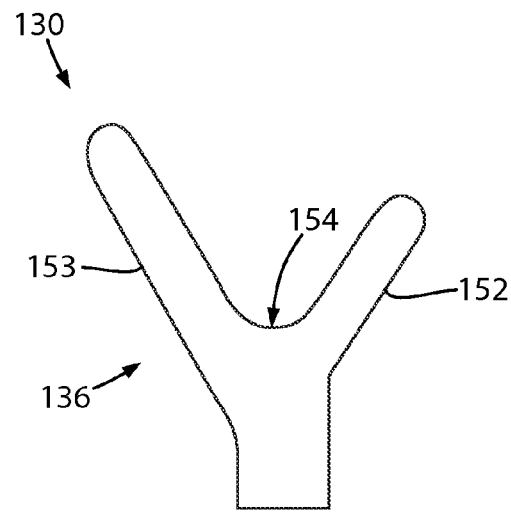
FIGS. 13-15 show alternative embodiments of polishing members.
Figures 14, 15:
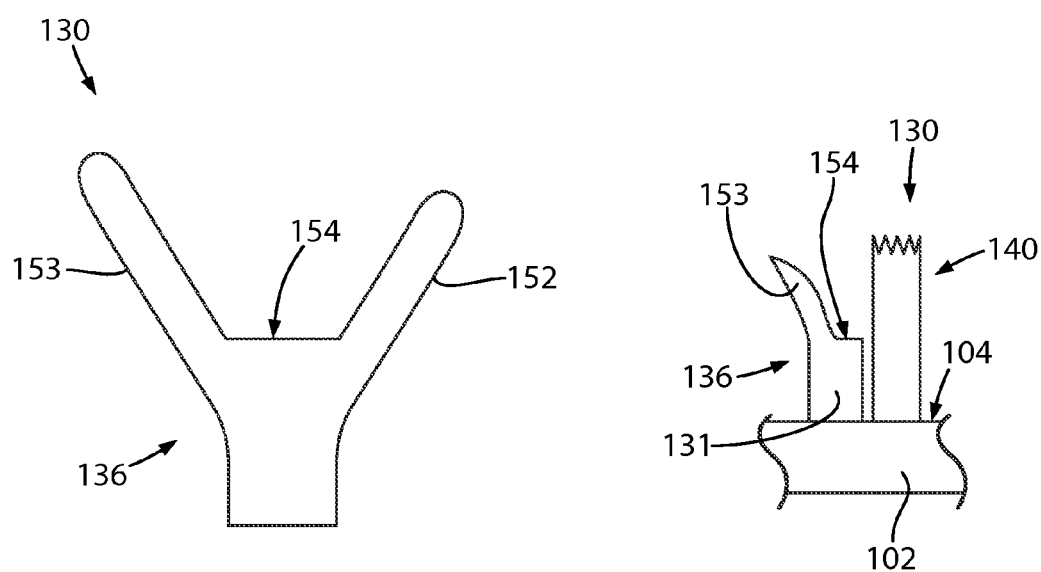

The bottom 154 of the dentifrice retaining recess 138 may have any suitable shape so long as dentifrice cannot escape through the lower portion of the retaining recess 138. In some embodiments, as shown in FIGS. 8 and 9, a closed bottom 154 may be relatively pointed or slightly rounded as shown at its lowermost point to eliminate stress concentration points which may lead to stress cracks induced by repetitious use of the toothbrush 100. In other embodiments, the closed bottom 154 may be more gradually and broadly rounded forming a V-shaped recess 138 having more of a flattened U-shape (see, e.g. FIG. 13). In yet other embodiments, the closed bottom 154 may be planar in portion (see, e.g. FIG. 14). In still yet other possible embodiments as shown in FIG. 15, the polishing element 136 may be formed without an inner branched portion 152 and a partially closed bottom 154 wherein the bristle element 140 functionally substitutes for the branched portion 152 by being abutted against or slightly spaced apart from the supporting base 131 to retain the dentifrice and prevent excesses outwards leakage of dentifrice downwards towards the front brushing side 104 of the toothbrush head 102. Accordingly, the invention is not limited to any particular shape of the bottom 154 which may be completely or partially closed so long as the polishing unit 130 is configured to retain the dentifrice in the active brushing zone.

In some possible embodiments, the branched portions 152, 153 may have the same or different vertical heights H1, H2 (shown in FIG. 8) with respect to each other as measured from a common point at the lowest point of the bottom 154 in the dentifrice retaining recess 138. Preferably, the outer branched portion 153 has a height H1 that is at least about the same height as but not less than the height H2 of the inner branched portion 152 to prevent excessive amounts of the dentifrice D from migrating or escaping radially outwards during brushing from polishing element 130, and then downwards out of the active brushing zone towards front brushing side 104 of the toothbrush head 102 in between the tooth cleaning element 120 where the effectiveness of the dentifrice for cleaning and polishing is lost. Also, preferably, the vertical depth of the dentifrice retaining recess 138 defined by the heights H1, H2 of the branched portions 152, 153 should be deep enough to hold and retain a sufficient amount of the dentifrice D to be effective for cleaning and polishing the teeth.

Figure 10:
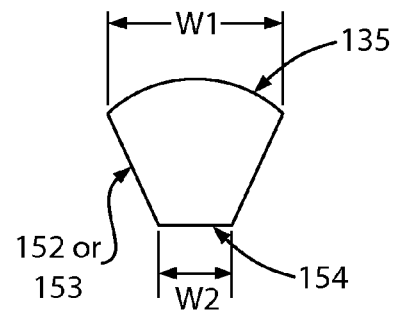
FIG. 10 is a frontal view of branched portions of the polishing member of FIG. 9.
Figure 11:
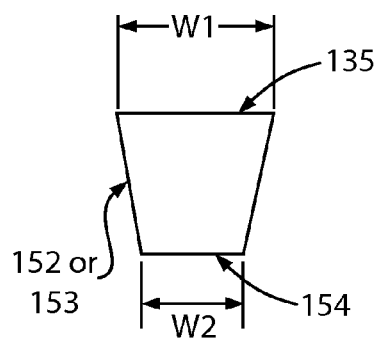
FIG. 11 is a frontal view of alternative branched portions of the polishing member of FIG. 9.

As best shown in FIGS. 8-11, each branched portion 152, 153 has a top width W1 measured between the outermost points on upper free end 135 and a bottom width W2 measured between the outermost points on lower base and 134. Each branched portion 152, 153 is horizontally widened preferably having a top width W1 that is larger than the corresponding respective thickness T1 or T2 of each portion (see FIGS. 10-11). Preferably, the top width W1 is larger than the bottom width W2 so that the upper free end 135 of branched portions 152, 153 flare horizontally outwards in relation to a narrow bottom width W2. This allows the upper free ends 135 of each polishing member 137 to be canted or angled outwards while keeping the gaps 157 relatively narrow to prevent excessive leakage of dentifrice outwards between polishing members (see, e.g. FIGS. 6-9). FIGS. 10 and 11 show two possible variations of the branched portions 152, 153 wherein the upper free end 135 of one or both branched portions may be arcuately shaped in FIG. 10 or alternatively straight in FIG. 11. Other possible free end configurations are possible.

It will be appreciated that the height H1, H2 of the branched portions 152, 153 along with the angle A1 formed therebetween should be selected so that the retaining recess 138 is deep enough and not so flat that the dentifrice D would tend to be easily slide off and become dislodged from the recess during the brushing action. It is well within the ambit of those skilled in the art to determine suitable parameters for H1, H2, and A1 without undue experimentation.

Referring now to FIGS. 2-3 and 6-7, the bristle element 140 is preferably disposed at least partially inside the polishing element 136, and more preferably completely inside the element 136 in aperture 139. The bristle element 140 may be formed as a bristle tuft having a generally vertical orientation in an exemplary embodiment extending upwards from the front brushing side 104 of the toothbrush head 102. Other suitable shapes are possible however. The bristle element 140 has a lower end (not shown) attached to the front brushing side 104 of the toothbrush head 102 and preferably is vertically higher than at least the inner branched portion 152 of each polishing member 137 with at least some of the individual bristles protruding vertically above the free end 135 of the branched portion 152 (see, e.g. FIG. 6). This arrangement enhances the cleaning effectiveness of the bristle element 140 especially for cleaning between the cusps of the premolars and molars and/or between the interdental spaces between the teeth. In other embodiments, the bristles of the bristle element 140 may protrude higher than the upper free ends 135 of both inner and outer branched portions 152, 153. In one embodiment, without limitation, the bristle element 140 may be circular (in top view) with relatively tightly packed bristles for improved reach and penetration into tight spaces between the teeth and/or tooth cusps. The bristles of the bristle element 140 may be tapered or non-tapered bristles.

It will be appreciated that other embodiments of the polishing unit 130 may have more or less polishing members 137 and other shaped bristle elements 140. Accordingly, the invention is not limited to the exemplary embodiments shown herein.

As best shown in FIG. 3, the polishing unit 130 is preferably centrally positioned in one embodiment between the lateral sides 106, 107 and along the longitudinal axis LA of the toothbrush head 102. In a preferred embodiment, the two axially aligned polishing units 130 may be provided with one unit being disposed between the transverse axis TA and the distal end 108 and another unit being disposed between the transverse axis TA and the proximal end 109.

The polishing unit 130 essentially forms a disc-shaped polishing pad for cleaning and polishing the teeth, which when accompanied by use of dentifrices having special cleaning, sensitivity protection and whitening agents is intended to provide more effective stain removal, sensitivity formula application, or whitening action. Advantageously, the dentifrice is well supported by retaining recess 138 in polishing heads 132 of the polishing unit 130 during brushing thereby reducing loss of dentifrice downwards between other tooth cleaning elements towards the front surface 104 of the toothbrush head 102 for more effective polishing, cleaning, sensitivity formula application and whitening action.

The operation of the toothbrush 100 and the polishing units 130 will now be briefly described with reference to the accompanying figures. The inactive pre-brushing position of the polishing unit 130 and the polishing element 136 is shown in FIGS. 6 and 9. The user first places a ribbon of dentifrice such as toothpaste on cleaning elements 120. At least a portion of the dentifrice becomes embedded in retaining recess 138 (see, e.g. FIG. 9). Alternative, a user applies a dentifrice directly to the teeth using an applicator. During brushing when a user presses the toothbrush head 102 against the teeth, the applied force F to the head will cause the flared inner and outer branched portions 152 and 153 of each polishing member 137 to elastically deform inwards and outwards respectively (see directional arrows, FIG. 9) tending to slightly flatten the polishing element 136 and dentifrice retaining recess 138. A majority of the dentifrice, either pre-applied to the toothbrush head or pre-applied to the user's teeth, advantageously will remain in position on each polishing unit 130 longer than in conventional toothbrushes by being trapped between bottom 154 of the retaining recess 138 and the teeth. Outwards and downwards leakage of dentifrice is beneficially minimized so more dentifrice remains available in the active brushing zone of the tooth cleaning elements 120 for a longer period of time for application directly to the teeth. This maximizes contact time of the dentifrice with the teeth to optimize the oral care benefits provided by the active ingredients of the dentifrice being used. Simultaneously, the branched portions 152 and 153 with their cleaning and dentifrice polishing surfaces 150 and 151 formed thereon will contact the teeth to provide cleaning, polishing, sensitivity application and/or whitening action in conjunction with the dentifrice. When the user removes the brushing pressure F from toothbrush head 102 (generally normal to the toothbrush head and teeth surfaces), the elastomeric polishing element 136 and individual polishing members 137 will return to their previous inactive position.

Referring to FIGS. 1-5, the polishing unit 130 is preferably at least partially surrounded by bristle elements that flank the circumferential sides of each polishing unit. In some embodiments, at least two and more preferably three or more arcuate tooth cleaning bristle elements 170 (in top or horizontal cross section) may be provided each having a concave inner side that faces towards and partially surrounds polishing unit 130. In one embodiment, four arcuate tooth cleaning elements 170 may be provided as shown.

Figure 2:
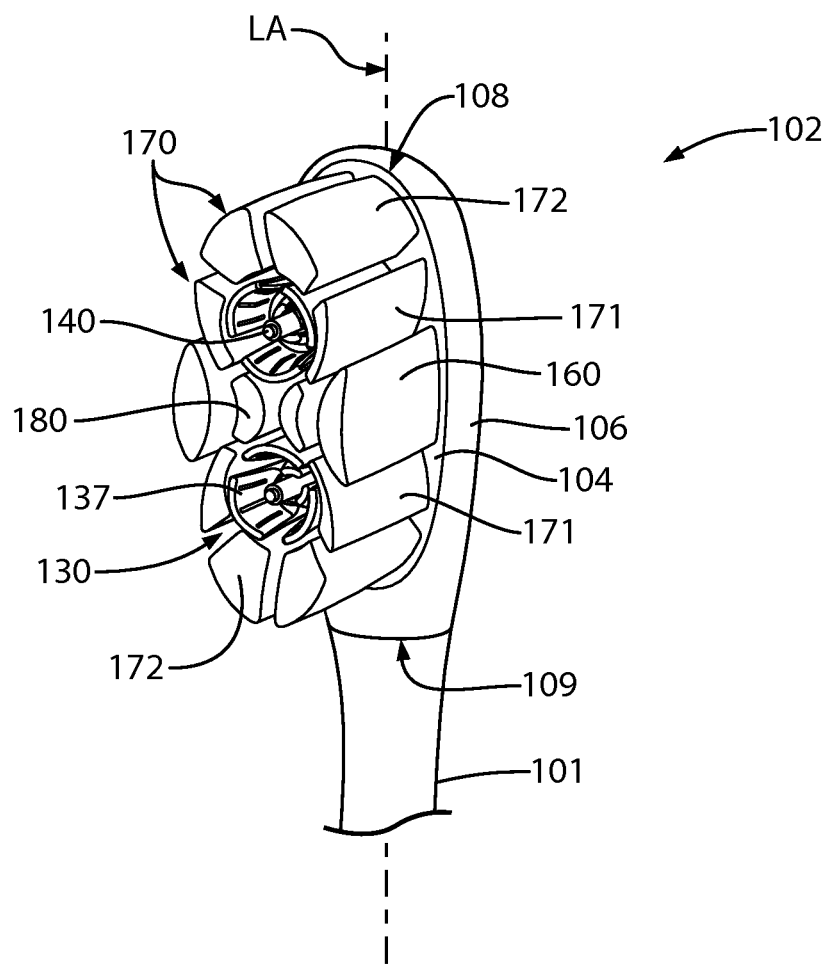
FIG. 2 is a perspective view of a toothbrush head thereof.

Each arcuate bristle element 170 is formed of a tuft of bristles made of any suitable bristle material conventionally used in the art and may be tapered or non-tapered. The arcuate bristle elements 170 may include a pair of transversely spaced apart lateral side arcuate elements 171 with one each located adjacent the polishing unit 130 near the peripheral edges and the lateral sides 106 and 107 of the toothbrush head 102, and at least one arcuate axial distal or proximal element 172 positioned along the longitudinal axis LA of head 102. In a preferred embodiment, two transversely spaced apart axial distal and proximal elements 172 are provided as shown. As best shown in FIGS. 2 and 3, one pair of axial distal element 172 is preferably located near the distal end 108 of the toothbrush head 102 (forward of the distal tooth polishing unit 130) and another pair of axial proximal element 172 is preferably located near the proximal end 109 of the toothbrush head 102 (rearward of the proximal tooth polishing unit 130 towards the handle 103). In a preferred bristle arrangement, the lateral and axial bristle elements 171, 172 are positioned symmetrically with respect to the longitudinal axis LA as shown in FIG. 3. In other possible arrangements, asymmetrical positioning of the bristle elements 171, 172 may be used.

With continuing reference to FIGS. 1-5, the proximal and/or distal axial bristle elements 172 may be angled or tapered such that the height of bristles gradually slopes in a longitudinal upwards direction away from transverse axis TA and towards the distal end 108 and the proximal end 109 of the toothbrush head 102, respectively, as best shown in FIG. 4. The angled arrangement of the axial bristle elements 172 enhances the reach and cleaning of these bristle tufts. The lateral side arcuate elements 171 may also be slanted or angled upwards in a longitudinal direction away from transverse axis TA and the proximal or distal ends 108, 109 of the toothbrush head 102 in some embodiments.

Referring to FIGS. 1-5, the toothbrush head 102 further includes a pair of intermediate tooth cleaning bristle elements 180 which are laterally spaced apart along the transverse axis TA in one preferred embodiment. Each intermediate bristle element 180 is preferably positioned between the longitudinal axis LA and the lateral sides 106 and 107 respectively, and more preferably is positioned between the longitudinal axis LA and the side cleaning elements 160 further described herein near the center of the toothbrush head 102 at the intersection of the longitudinal axis LA and the transverse axis TA. In one exemplary arrangement, the intermediate bristle elements 180 may be formed as arcuately-shaped elements (in lateral horizontal cross section) with a concave side facing outward away from the longitudinal axis LA towards the sides 106 or 107. The bristle elements 180 are axially disposed between the polishing units 130, but preferably offset from the longitudinal axis LA as shown. In one exemplary embodiment, the bristle elements 180 are oriented and arranged on the toothbrush head 102 to coordinate with the concavely inward shapes of the arcuate bristle elements 170 to form a "figure eight or 8" pattern when viewed from above (see FIG. 3). The intermediate bristle elements 150 may be comprised of a tuft of bristles formed of any suitable material conventionally used in the art.

Referring to FIGS. 1-5, side cleaning bristle elements 160 may further be provided and supported by the toothbrush head 102. In one exemplary embodiment, the side cleaning bristle elements 160 may have one convex side (in top view or lateral horizontal cross section) that faces inwards towards longitudinal axis LA and complements the outward facing concave side of intermediate bristle elements 180 to fill the space or void between the intermediate elements and the laterals sides 106 and 107 of the toothbrush head 102. In one embodiment, one side bristle element 160 is provided proximate to each later side 106, 107 on the toothbrush head 102, and preferably may be positioned on the transverse axis TA. In some embodiments, the side cleaning bristle elements 160 may each be formed from two bristle tufts split along the transverse axis TA but retaining the combined convex shape on one side. Exemplary embodiments of the side cleaning bristle elements 160 may be designed for deep cleaning having a vertical height that is higher than at least adjacent intermediate bristle elements 180 to enhance cleaning of the teeth along the gum line. It will be appreciated that other numbers of and/or arrangements of side bristle elements 160 are possible.

In some embodiments for applications with users having sensitive teeth, some or all of bristle elements 160, 170 and/or 180 may be tapered and of a softer bristle material than other bristle elements which may be non-tapered and made of a relatively stiffer material. In one possible construction, the axial distal and proximal bristle elements 172 and side cleaning elements 160 may be made of a softer bristle material for gentle interdental cleaning and reduce friction along the gum line than other tooth cleaning bristle elements on the toothbrush head 102.

The tooth cleaning elements described herein may be attached to the toothbrush head by any suitable conventional method used in the art such as, without limitation for example, in mold tufting (IMT), anchor free tufting (AFT), anchored/stapled, injection molding, ultrasonic welding, and combinations thereof. In addition, features of the exemplary embodiments described herein may be practiced and incorporated in manual or powered toothbrushes.

The devices and apparatuses described herein utilize conventional, commercially-available components which will be readily known to and obtainable by those skilled in the art. Therefore, it is well within ambit of those skilled in the art to assemble such components to create these devices and to employ the methods described herein for the detection and treatment of oral conditions related to the presence of bacteria or bacterial metabolic products without undue experimentation.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

The invention claimed is:

1. An oral care implement comprising:
a toothbrush head; and
a plurality of tooth cleaning elements supported by the toothbrush head, the tooth cleaning elements including at least a first tooth polishing unit, the first tooth polishing unit having an elastomeric polishing element including an elevated dentifrice retaining recess spaced above the toothbrush head for holding dentifrice, wherein the elastomeric polishing element is comprised of a plurality of Y-shaped polishing members that are arranged concentrically on the toothbrush head in a spaced apart manner about a central point, each said Y-shaped polishing member having an outer branched portion and an inner branched portion defining at least part of the elevated dentifrice retaining recess, the outer branched portion being radially outward of the inner potion.

2. The oral care implement of claim 1, wherein the elastomeric polishing element defines a central aperture, and wherein the first tooth polishing unit further comprises a bristle element disposed inside the central aperture of the elastomeric polishing element.

3. The oral care implement of claim 1, wherein the retaining recess is shaped as an annular groove having an upwardly open top for receiving the dentifrice.

4. The oral care implement of claim 3, wherein the retaining recess includes a bottom that is at least partially closed for retaining the dentifrice.

5. The oral care implement of claim 1, wherein the retaining recess defines a tooth polishing surface including a plurality of ribs.

6. The oral care implement of claim 1, further comprising a second tooth polishing unit.

7. The oral care implement of claim 6, wherein the toothbrush head comprises two opposing lateral sides and a longitudinal axis positioned between the two opposing lateral sides, and wherein the first and second tooth polishing units are axially aligned on the longitudinal axis of the toothbrush head.

8. The oral care implement of claim 1, wherein the retaining recess is V-shaped in vertical cross section.

9. The oral care implement of claim 1, wherein the retaining recess includes an upward facing open top and a closed bottom.

10. The oral care implement of claim 9, wherein the outer branched portion of each polishing member flares outwardly away from the central point and wherein the opposing inner branched portion of each polishing member flares inwardly towards the central point.

11. A toothbrush comprising:
a toothbrush head having a front side, a rear side, two opposing lateral sides and a longitudinal axis positioned between the two opposing lateral sides; and
a plurality of tooth cleaning elements supported by the toothbrush head, the tooth cleaning elements including at least one tooth polishing unit comprising an elastomeric polishing element and a bristle element disposed at least partially inside the elastomeric polishing element, the elastomeric polishing element having an elevated dentifrice retaining recess spaced above the toothbrush head for holding dentifrice, wherein the elastomeric polishing element is comprised of a plurality of Y-shaped polishing members, each said Y-shaped polishing member having an outer branched portion and an inner branched portion defining at least part of the elevated dentifrice retaining recess, the outer branched portion being radially outward of the inner branched portion, and wherein the tooth polishing unit is positioned along the longitudinal axis of the toothbrush head.

12. The toothbrush of claim 11, wherein the bristle element extends vertically above the elastomeric polishing element.

13. The toothbrush of claim 11 wherein the longitudinal axis is located centrally on the toothbrush head equi-distant from each of the two opposing lateral sides of the toothbrush head.

14. A toothbrush comprising:
a toothbrush head defining a longitudinal axis;
a plurality of tooth cleaning elements supported by the toothbrush head, the tooth cleaning elements including at least one tooth polishing unit comprising an elastomeric polishing element and a bristle element disposed at least partially inside the elastomeric polishing element, the elastomeric polishing element having an elevated dentifrice retaining recess spaced above the toothbrush head for holding dentifrice, wherein the elastomeric polishing element is comprised of a plurality of Y-shaped polishing members; and
wherein the elastomeric polishing element includes a plurality of outwardly flared branched portions and opposing inwardly flared branched portions arranged circumferentially around a central aperture, the outwardly flared branched portions being radially outward of the inwardly flared branched portions, the branched portions defining the dentifrice retaining recess.

15. The toothbrush of claim 14, wherein the bristle element is disposed in the central aperture.

16. The toothbrush of claim 15, wherein the bristle element has a circular shape in top view.

17. A toothbrush comprising:
a toothbrush head defining a longitudinal axis;
a plurality of tooth cleaning elements supported by the toothbrush head, the tooth cleaning elements including at least one tooth polishing unit comprising an elastomeric polishing element and a bristle element disposed at least partially inside the elastomeric polishing element, the elastomeric polishing element having an elevated dentifrice retaining recess spaced above the toothbrush head for holding dentifrice, wherein the elastomeric polishing element is comprised of a plurality of Y-shaped polishing members; and
wherein the tooth cleaning elements further include a plurality of arcuately shaped bristle elements arranged on the toothbrush head to define a "figure 8" pattern.

18. A toothbrush comprising:
a head defining a longitudinal axis and a front brushing side;
a plurality of bristle elements attached to the front brushing side of the head;
an elastomeric polishing element attached to the front brushing side of the head, the elastomeric polishing element being comprised of a plurality of individual polishing members, each polishing member having an elevated dentifrice retaining recess spaced above the toothbrush head for supporting dentifrice, wherein the polishing members are Y-shaped, each said Y-shaped polishing member having an outer branched portion and an inner branched portion defining at least part of the elevated dentifrice retaining recess, the outer branched portion being radially outward of the inner branched portion; and
wherein the polishing members are concentrically arranged around a central point to collectively define a circular shaped polishing element.

19. The toothbrush of claim 18, wherein the polishing members each include a polishing head and a supporting base attached to the toothbrush head, the polishing heads defining a V-shaped dentifrice retaining recess in each polishing member.

20. The toothbrush of claim 18, wherein the inner and outer branched portions define an opposing pair of spaced apart and upwardly extending branched portions that define a portion of the dentifrice retaining recess.

21. The toothbrush of claim 20, wherein the branched portions are joined at a common closed bottom and are arranged in upwardly diverging relationship to each other to form an open top of the dentifrice retaining recess.

22. The toothbrush of claim 18, wherein the dentifrice retaining recess has a closed bottom for supporting the dentifrice.

* * * * *